United States Patent [19]

Johnson

[11] Patent Number: 5,720,942
[45] Date of Patent: Feb. 24, 1998

[54] TWO-PHASE TANNING COMPOSITIONS AND METHODS RELATING THERETO

[75] Inventor: Geoffrey W.A. Johnson, Redmond, Wash.

[73] Assignee: Radical Products, Inc., Redmond, Wash.

[21] Appl. No.: 512,685

[22] Filed: Aug. 8, 1995

Related U.S. Application Data

[63] Continuation of Ser. No. 891,588, Jun. 1, 1992, abandoned.

[51] Int. Cl.$^6$ ............................... A61K 7/42; A61K 7/00
[52] U.S. Cl. ............................ 424/59; 424/60; 424/63; 424/64; 424/400; 424/401
[58] Field of Search ............................... 424/59, 60, 63, 424/64, 400, 401

[56] References Cited

U.S. PATENT DOCUMENTS

| | | | |
|---|---|---|---|
| 4,466,805 | 8/1984 | Welters et al. | 8/406 |
| 5,213,799 | 5/1993 | Goring et al. | 424/401 |
| 5,569,460 | 10/1996 | Kurz et al. | 824/59 |

OTHER PUBLICATIONS

Spalton, Lawrence M., *Pharmaceutical Emulsions and Emulsifying Agents*, Second Edition, The Chemist and Druggist, 1956, pp. 20–21.

*Primary Examiner*—Shelley A. Dodson
*Attorney, Agent, or Firm*—Seed and Berry

[57] ABSTRACT

The is disclosed a two-phase oil and water tanning composition which, when agitated, forms a single-phase, but readily converts back to two-phases upon settling. The oil and water phase of the tanning composition may be separately colored to create a visually pleasing and distinctive product. Formation of a single-phase upon agitation permits equal application of both the oil and water phases, regardless of the mode of application. Reversion to the two-phase oil and water composition upon settling imparts the desired product appearance after application.

22 Claims, No Drawings

TWO-PHASE TANNING COMPOSITIONS AND METHODS RELATING THERETO

CROSS-REFERENCE TO RELATED APPLICATION

This application is a continuation of U.S. patent application Ser. No. 07/891,588, filed Jun. 1, 1992, now abandoned.

TECHNICAL FIELD

The present invention is generally directed to a two-phase tanning composition and, more specifically, to a tanning composition which, when mixed to form a single phase, readily reverts to the two-phase composition.

BACKGROUND OF THE INVENTION

Mixtures of oil and water have previously been applied to the skin for use as tanning compositions. Such oil and water compositions will separate to form two-phases, with the denser water phase on bottom and the less dense oil phase on top. Prior to application, the user must thoroughly shake or agitate the two-phase product in an attempt to form a single oil-water phase. If such agitation is incomplete or if the single-phase oil-water mixture immediately reverts to two-phases, the user will apply more or less of one component. For example, when a user pores the mixture from a container, a greater quantity of the top-layer oil component is likely to be applied. Conversely, if spray application is employed, such applicators typically draw from the bottom of a spray bottle, and thus a greater quantity of the lower-layer water component is likely to be applied. In either instance, one component of the mixture is consumed faster than the other component.

In an attempt to ensure even application of all components of oil and water tanning compositions, some manufactures have added agents which form a stable oil and water emulsion. Such emulsions, however, are not particularly attractive to the consumer (especially when packaged in a clear container), and only allow the manufacturer a single color choice for the emulsion. In contrast, two-phase tanning compositions allow the manufacturer to utilized different coloring agents in both the top and bottom phases, and produce product color schemes which are visually attractive and distinctive to the consumer when packaged in a clear container. However, prior two-phase oil and water tanning products suffer the disadvantages discussed above.

Accordingly, there is a need in the art for an oil and water composition which, when mixed, will exist as a single phase for a period of time sufficient to permit simultaneous application of both the oil and water components and, upon settling, will readily revert to a two-phase product. The present invention satisfies this need, and provides further related advantages.

SUMMARY OF THE INVENTION

This invention is directed to a two-phase oil and water tanning composition which includes an oil component, a water component and a separation agent. The two-phase composition forms a single-phase mixture upon agitation, and separates to form the two-phase oil and water composition upon settling. The separation agent serves to control the period of time necessary to form the two-phase composition from the single-phase mixture following agitation.

In one embodiment, the two-phase tanning composition is formulated as a solution comprising an oil and a water component, and utilizes ethanol as the separation agent. In a related embodiment, the two-phase tanning composition is formulated as a lotion comprising an oil component and a water component, with methyl cellulose as the separation agent.

In a preferred embodiment, the two-phase oil and water tanning composition contains from 50–60% by weight water component, from 25–35% by weight oil component, and from 10–15% by weight separation agent (all weight percentages are based on the total weight of the composition). Optional ingredients may also be present in the oil and/or water components, including coloring agents and fragrances.

The present invention also discloses methods for controlling the separation time between the agitated, single-phase oil-water mixture and the two-phase oil and water composition by addition of a separation agent. Methods directed to manufacturing the two-phase oil and water compositions are also disclosed.

These and related aspects of the present invention will become evident upon reference to the following detailed description.

DETAILED DESCRIPTION OF THE INVENTION

The present invention discloses a two-phase tanning composition containing an oil component, a water component and a separation agent. The tanning composition exists as a two-phase product when undisturbed. However, upon agitation, the composition forms a single-phase oil and water mixture. The period of time necessary for the single-phase mixture to revert to two-phases is controlled by the separation agent. In the absence of the separation agent, mixtures of oil and water will instantly separate.

The separation agents of the present invention prevent instant separation of the oil and water components following agitation (such as shaking). If instant separation occurs, the user will apply an excess of either the oil or the water component. For example, a pump sprayer typically draws fluid from the bottom of the container through a tube internal to the container. In the absence of a separation agent, an agitated oil and water mixture will immediately separate into a lower water phase and an upper oil phase. Since the pump sprayer draws from the bottom of the container, the lower water phase will primarily be applied to the user's skin, rather than a proportional mixture of both the oil and water components. After several applications, the ratio of oil to water will change, eventually leaving just an oil phase in the container. Conversely, if an oil and water mixture is poured from a container, the upper oil phase will be applied at a greater rate than the lower water phase. In either case, the oil and water components will not be applied to the skin in a portion equal to the ratio of oil to water initially present in the container.

In one embodiment of the present invention, the two-phase tanning composition may be formulated as a solution for application by, for example, a pump sprayer. The separation agent for this application is preferably an alcohol, and more preferably ethanol. By adding an appropriate amount of ethanol to the oil and water composition, the separation time may be controlled.

In a related embodiment, the two-phase tanning composition may be formulated for application as a lotion or gel. The separation agent for this application is preferably a methylcellulose (e.g., methylcellulose, hydroxypropyl methylcellulose, and sodium carboxy methylcellulose). Again, by adding an appropriate amount of methylcellulose to the oil and water composition, the separation time may be controlled.

The separation agent of the present invention must be present in an amount which delays reversion of the agitated, single-phase, oil and water mixture for a period of time sufficient to permit application of the mixture to the user's skin. However, the separation agent must not be present in an amount which prevents the subsequent separation of the single-phase oil and water mixture to the two-phase composition. Rather, the separation agent must aid in the temporary emulsification of the oil and water phases for a relatively short period of time. Preferably, the separation agent will delay separation (i.e., from the agitated, single-phase, oil and water mixture to the two-phase, oil and water composition) for the solution formulation for 1–10 minutes, and more preferably from 1–5 minutes. With regard to the lotion or gel formulation, the separation agent is preferably present in an amount sufficient to delay separation for 10 minutes to 2 hours, and more preferably from 1–2 hours. This separation delay allows the user sufficient application time following agitation to apply the single-phase oil and water mixture to the skin, but permits reversion to the desired two-phase product in a sufficiently shod period of time following application.

The water component may be present in the two-phase composition in an amount ranging from 1–93% by weight, the oil component may be present in an amount ranging from 1–93% by weight, and the separation may be present in an amount ranging from 6–30% by weight. For commercial tanning products, the water component is preferably 40–70% by weight, more preferably 50–60% by weight, and most preferably about 55% by weight. Depending on the region of the country where the product is sold, the water to oil ratio may vary within the above ranges, depending upon consumer preference. Preferably, the separation agent is present in an amount ranging from 10–20% by weight, and may be varied depending upon the desired delay in separation.

In a preferred embodiment, the two-phase tanning composition includes from 50–60% by weight water component, from 25–35% by weight oil component, and from 5–15% by weight separation agent; and more preferably from 50–55% by weight water component, from 30–35% by weight oil component, and from 0–15% by weight separation agent; and most preferably 55% by weight water component, 31% by weight oil component, and 14% by weight separation agent.

The separation agents of the present invention are water soluble, and are present in the water component of the two-phase oil and water tanning composition. In addition, the water component preferably contains one or more coloring agents or dies to impart the desired color to the water phase of the two-phase tanning composition. Suitable water soluble coloring agents include, but are not limited to, D&C blue #1, FD&C red #4, D&C green #5, #6, #8, D&C orange #4, D&C red #17, #22, #28, #33, #39, D&C violet #2, D&C yellow #7, #8, #10 and #11. The coloring agent is present in the water component in an amount sufficient to impart the desired color.

Additional water-soluble components may also be present in the water phase. For example, tanning accelerators, such as L-tyrosine, vitamin B-6 and riboflavin (e.g., UNIPERTAN P-24, Lipo Chemical Company), are water soluble, and may be employed in the tanning compositions of the present invention. Similarly, water-soluble sun screens and fragrances may be utilized also be present. To prevent freezing, the water component of the tanning composition may include an anti-freeze agent, such as propylene glycol. Additional ingredients, such as NaPCA (i.e., shark liver oil) and Aloe Vera juice, may also be present in the water component in amounts which are determined by user preference. Such additional water-soluble components should not cloud or emulsify the two-phase tanning composition.

The oil component of the two-phase tanning composition may contain a single oil or a mixture of two or more different oils. Suitable oils include, but are not limited to: mineral oil (i.e., liquid petrolatum, density of approximately 0.8 to 0.9; also referred to as octyl palmitate); tropical oils, including oil of avocado, oil of almond, oil of apricot, oil of camellia, oil of macadamia, oil of meadowfoam, oil of kukui, oil of sesame; animal oils, such as mink oil; and silicon fluid (e.g., dimethicone, Union Carbide Corp.; cyclomethacone, Dow Chemical Co.). The above oils may be employed in any ratio, and may be modified depending upon the desired end product. For example, since mineral oil generally "feels more oily" to the user, the relative proportion of silicon gel may be increased to impart a "less oily" feel to the final product. Similarly, cost considerations and user preference may also control the relative proportions of the ingredients within the oil component. In a preferred embodiment, the oil component is present in a weight ratio of mineral oil to silicon fluid to tropical oil of 20:10:1, respectively.

Oil-soluble coloring agents are preferably added to the oil component to impart the desired color. Preferred oil-soluble coloring agents include, but are not limited to, D&C green #6, D&C red #17, D&C yellow #11 and D&C violet #2. Optional oil-soluble components may also include appropriate fragrances and sun screens, providing such ingredients do not cloud or emulsify the two-phase tanning composition.

By packaging the two-phase tanning composition in a clear container, and coloring the oil component and water component differently, a distinctive and visually appealing product is obtained. In manufacturing the two-phase tanning composition of the present invention, the water component and oil component are first separately formed by combining their respective ingredients. Appropriate containers (e.g., clear bottles) are then partially filled with the water component, preferably using an appropriate filling machine employing multiple filling heads. The containers are then filled with the oil component in a manner which provides a definite two-phase split line between the upper oil component and the lower water component.

The following examples are offered by way of illustration and not limitation.

EXAMPLE 1

Two-Phase Tanning Solution

Oil component
20% by weight mineral oil (i.e., octyl palmitate)
10% by weight silicon fluid (i.e., dimethicone)
1% by weight tropical oils (i.e., mixture of oil of avocado, oil of almond, oil of macadamia, oil of meadowfoam, oil of kukui and oil of sesame)
q.s.* D&C red #17
q.s. oil-soluble flagrance
(*q.s.=quantity sufficient)
Water Component
55% by weight water
14% by weight ethanol
q.s. D&C red #33
0.05% by weight NaPCA
q.s. fragrance

EXAMPLE 2

Two-Phase Tanning Lotion

Oil component
20% by weight mineral oil (i.e., octyl palmitate)

10% by weight silicon fluid (i.e., dimethicone)

1% by weight tropical oils (i.e., mixture of oil of avocado, oil of almond, oil of macadamia, oil of meadowfoam, oil of kukui and oil of sesame)

q.s. D&C violet #2 q.s. oil-soluble fragrance

Water Component

55% by weight water 0.5% by weight Aloe Vera juice

14% by weight methylcellulose q.s. D&C blue #1

0.05% by weight NaPCA q.s. water-soluble fragrance

From the foregoing, it will be appreciated that, although specific embodiments of the invention have been described herein for purpose of illustration, various modifications may be made without deviation from the spirit and scope of the invention.

I claim:

1. A two-phase oil and water tanning composition, comprising (a) from 1% to 93% by weight of an oil component selected from mineral oil, tropical oil, animal oil, silicon fluid or mixtures thereof, (b) from 1% to 93% by weight of a water component, and (c) from 6% to 30% by weight of a separation agent selected from methylcellulose and alcohol, wherein the two-phase oil and water composition forms a single-phase oil-water mixture upon agitation, and separates to form the two-phase oil and water composition upon settling, and wherein the separation agent controls the period of time necessary to form the two-phase composition from the single-phase mixture.

2. The composition of claim 1 wherein the water component is present in an amount ranging from 50% to 60% by weight based on the total weight of the composition.

3. The composition of claim 1 wherein the oil component is present in an amount ranging from 25% to 35% by weight based on the total weight of the composition.

4. The composition of claim 1 wherein the separation agent is present in an amount ranging from 10% to 15% by weight based on the total weight of the composition.

5. The composition of claim 1 wherein the oil component is selected from the group consisting of mineral oil, silicon fluid and tropical oils.

6. The composition of claim 1 wherein the separation agent is ethanol.

7. The composition of claim 6 wherein the ethanol is present in an amount sufficient to delay separation of the agitated single-phase oil-water mixture to the two-phase oil and water composition by 1 minute to 10 minutes.

8. The composition of claim 1 wherein the separation agent is methylcellulose.

9. The composition of claim 8 wherein the methylcellulose is present in an amount sufficient to delay separation of the agitated single-phase oil-water mixture to the two-phase oil and water composition by 10 minutes to 2 hours.

10. The composition of claim 1 further including at least one coloring agent in the oil component, water component, or both the oil and water components.

11. A two phase tanning solution, comprising about 31% by weight of an oil component selected from mineral oil, tropical oil, animal oil, silicon fluid or mixtures thereof, about 55% by weight of a water component, and about 14% by weight of ethanol, wherein the two-phase tanning solution forms a single-phase oil-water mixture upon agitation, and separates to form the two-phase tanning solution upon settling.

12. The composition of claim 11 further including at least one coloring agent in the oil component, water component, or both the oil and water components.

13. The solution of claim 11 wherein the oil component comprises about 20% by weight mineral oil, about 10% by weight silicon fluid and about 1% by weight tropical oils based on the weight of the total solution.

14. A two-phase tanning lotion, comprising about 31% by weight of an oil component selected from mineral oil, tropical oil, animal oil, silicon fluid or mixtures thereof, about 55% by weight of a water component, and about 14% by weight of methylcellulose, wherein the two-phase tanning lotion forms a single-phase oil-water mixture upon agitation, and separates to form the two-phase tanning lotion upon settling.

15. The composition of claim 14 further including at least one coloring agent in the oil component, water component, or both the oil and water components.

16. The solution of claim 14 wherein the oil component comprises about 20% by weight mineral oil, about 10% by weight silicon fluid and about 1% by weight tropical oils based on the weight of the total solution.

17. A method for controlling the separation time between an agitated single-phase oil-water mixture and a two-phase oil and water composition, wherein the oil is selected from mineral oil, tropical oil, animal oil, silicon fluid or mixtures thereof, and wherein the oil of the oil-water mixture and the oil and water composition is present in an amount ranging from 1% to 93% by weight and the water is present in an amount ranging from 1% to 93% by weight, the method comprising adding a water-soluble separation agent to the water component of the oil and water mixture in an amount sufficient to delay separation for a period of time ranging from 1 minute to 2 hours, wherein the separation agent is methylcellulose or alcohol and is added in an amount ranging from 6% –30% by weight.

18. The method of claim 17 wherein the separation agent is ethanol.

19. The method of claim 18 wherein the ethanol is added in an amount sufficient to delay separation for a period of time ranging from 1 minute to 10 minutes.

20. The method of claim 17 wherein the separation agent is methylcellulose.

21. The method of claim 20 wherein the methylcellulose is added in an amount sufficient to delay separation for a period of time ranging from 10 minutes to 2 hours.

22. A method for manufacturing a two-phase oil and water composition, comprising:

admixing water with a separation and a first coloring agent to form a colored water component, where the separation agent is selected from methylcellulose or alcohol;

adding the colored water component to a clear container;

admixing oil with a second coloring agent to form a colored oil component, wherein the oil is selected from mineral oil, tropical oil, animal oil, silicon fluid or mixtures thereof; and adding the colored oil component to the container under limited agitation such that the colored water component and the colored oil component exist as two-phases within the container, wherein the resulting two-phase oil and water composition comprise from 1% to 93% by weight of oil, from 1% to 93% by weight of water, and from 6% to 30% by weight of the separation agent.

* * * * *